US008428712B2

(12) United States Patent
Davis et al.

(10) Patent No.: US 8,428,712 B2
(45) Date of Patent: Apr. 23, 2013

(54) CONCURRENT DELIVERY OF TREATMENT THERAPY WITH TELEMETRY IN AN IMPLANTABLE MEDICAL DEVICE

(75) Inventors: Timothy J. Davis, Coon Rapids, MN (US); Leroy L. Perz, Buffalo, MN (US); Nathan A. Torgerson, Andover, MN (US); Carl D. Wahlstrand, Lino Lakes, MN (US); David W. Hoffman, Inver Grove Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 947 days.

(21) Appl. No.: 11/185,525

(22) Filed: Jul. 20, 2005

(65) Prior Publication Data
US 2006/0020306 A1 Jan. 26, 2006

Related U.S. Application Data

(60) Provisional application No. 60/589,950, filed on Jul. 21, 2004, provisional application No. 60/589,393, filed on Jul. 20, 2004.

(51) Int. Cl.
*A61N 1/00* (2006.01)
*A61K 9/22* (2006.01)

(52) U.S. Cl.
USPC ........ 607/5; 607/32; 607/33; 607/60; 607/61; 604/891.1

(58) Field of Classification Search ............... 604/891.1; 128/903; 607/32–33, 60–61
See application file for complete search history.

(56) References Cited

U.S. PATENT DOCUMENTS

| 3,357,434 | A | 12/1967 | Abell |
| 3,888,260 | A | 6/1975 | Fischell |
| 4,071,032 | A | 1/1978 | Schulman |
| 4,134,408 | A | 1/1979 | Brownlee et al. |
| 4,186,749 | A | 2/1980 | Fryer |
| 4,237,895 | A | 12/1980 | Johnson |
| 4,373,527 | A | 2/1983 | Fischell |
| 4,550,370 | A | 10/1985 | Baker |
| 4,562,841 | A | 1/1986 | Brockway et al. |

(Continued)

FOREIGN PATENT DOCUMENTS

| EP | 0 472 411 | 2/1992 |
| EP | 1 048 324 | 11/2000 |

(Continued)

OTHER PUBLICATIONS

International Search Report received from the European Patent Office, dated Nov. 2, 2005, 6 pages.

(Continued)

*Primary Examiner* — Mark W Bockelman
(74) *Attorney, Agent, or Firm* — Beth L. McMahon; IPLM Group, P.A.

(57) ABSTRACT

A system, method and implantable medical for concurrently providing a therapeutic output to a patient while communicating transcutaneously with an external device. The therapeutic output is provided to the patient with an implantable medical device wherein an electromagnetic signal is associated with at least one of recharging of a rechargeable power source and providing the therapeutic output. Bi-directional transcutaneous communication is conducted via via telemetry between the implantable medical device and an external device using a telemetry signal while the telemetry signal and the electromagnetic signal occur simultaneously.

38 Claims, 10 Drawing Sheets

U.S. PATENT DOCUMENTS

| | | | |
|---|---|---|---|
| 5,113,869 A | 5/1992 | Nappholz et al. | |
| 5,279,292 A | 1/1994 | Baumann et al. | |
| 5,314,453 A | 5/1994 | Jeutter et al. | |
| 5,314,457 A | 5/1994 | Jeutter et al. | |
| 5,354,319 A | 10/1994 | Wyborny et al. | |
| 5,411,537 A | 5/1995 | Munshi et al. | |
| 5,562,713 A * | 10/1996 | Silvian | 607/32 |
| 5,613,935 A | 3/1997 | Jarvik | |
| 5,630,836 A * | 5/1997 | Prem et al. | 607/61 |
| 5,690,693 A | 11/1997 | Wang et al. | |
| 5,713,939 A | 2/1998 | Nedungadi et al. | |
| 5,733,313 A | 3/1998 | Barreras et al. | |
| 5,769,877 A * | 6/1998 | Barreras, Sr. | 607/61 |
| 5,938,691 A | 8/1999 | Schulman et al. | |
| 5,991,664 A | 11/1999 | Seligman | |
| 6,067,474 A | 5/2000 | Schulman et al. | |
| 6,154,677 A | 11/2000 | Leysieffer | |
| 6,275,737 B1 | 8/2001 | Mann | |
| 6,308,101 B1 | 10/2001 | Faltys et al. | |
| 6,324,430 B1 | 11/2001 | Zarinetchi et al. | |
| 6,505,077 B1 | 1/2003 | Kast et al. | |
| 6,516,227 B1 | 2/2003 | Meadows et al. | |
| 6,553,263 B1 * | 4/2003 | Meadows et al. | 607/61 |
| 6,562,001 B2 * | 5/2003 | Lebel et al. | 604/65 |
| 6,622,044 B2 * | 9/2003 | Bange et al. | 607/27 |
| 6,699,187 B2 | 3/2004 | Webb et al. | |
| 6,766,200 B2 * | 7/2004 | Cox | 607/60 |
| 7,177,698 B2 * | 2/2007 | Klosterman et al. | 607/60 |
| 2001/0037366 A1 | 11/2001 | Webb et al. | |
| 2003/0065370 A1 | 4/2003 | Lebel et al. | |
| 2003/0139783 A1 | 7/2003 | Kilgore et al. | |
| 2003/0149459 A1 | 8/2003 | Von Arx et al. | |
| 2004/0059392 A1 | 3/2004 | Parramon et al. | |

FOREIGN PATENT DOCUMENTS

| | | |
|---|---|---|
| WO | WO 98/37926 | 11/1998 |
| WO | WO 99/06108 | 2/1999 |
| WO | WO 99/44684 | 9/1999 |
| WO | WO 00/01442 | 1/2000 |
| WO | WO 00/04945 | 2/2000 |
| WO | WO 01/83029 | 11/2001 |
| WO | WO 01/97908 | 12/2001 |
| WO | WO 03/033070 | 4/2003 |

OTHER PUBLICATIONS

International Search Report from PCT/US2005/025665, mailed by the European Patent Office on Nov. 15, 2005 (4 pgs.).

Medtronic, Inc. "Mattrix Neurostimulation System", Brochure, 1995.

Medtronic, Inc. "Implantable Neurostimulation Systems", 1998.

* cited by examiner

"1"    "0"

"1"    "0"

CONCURRENT DELIVERY OF TREATMENT THERAPY WITH TELEMETRY IN AN IMPLANTABLE MEDICAL DEVICE

RELATED APPLICATION

This application claims priority to provisional U.S. application Ser. No. 60/589,393, filed Jul. 20, 2004, and provisional U.S. application Ser. No. 60/589,950, filed Jul. 21, 2004.

FIELD OF THE INVENTION

The present invention relates generally to implantable medical devices and, more particularly, to implantable medical devices providing a therapeutic electrical output and transcutaneous telemetry.

BACKGROUND OF THE INVENTION

Implantable medical devices for producing a therapeutic result in a patient are well known. Examples of such implantable medical devices include implantable drug infusion pumps, implantable neurostimulators, implantable cardioverters, implantable cardiac pacemakers, implantable defibrillators and cochlear implants. Some of these devices, if not all, and other devices either provide an electrical output or otherwise contain electrical circuitry to perform their intended function.

It is common for implantable medical devices, including implantable medical devices providing an electrical therapeutic output, to utilize transcutaneous telemetry to transfer information to and from the implanted medical device. Information typically transferred to an implanted medical device includes transferring instructions or programs to the implanted medical device from an external device such as an external programmer. Information typically transferred from an implanted medical includes information regarding the status and/or performance of the implanted medical device.

Existing implantable medical devices and/or external programmers, such as typical neurological stimulators, can not receive telemetry when the implantable medical device is providing therapy. The noise generated by creating electrical stimulation therapy pulses and the pulses themselves can be coupled onto the telemetry receiving antenna and the resulting noise can prevent the telemetry signal from being received. In implantable stimulators such as the Itrel 3™ stimulator, Synergy™ stimulator, and Kinetra™ stimulator manufactured by Medtronic, Inc., Minneapolis, Minn., the telemetry receiver is turned on briefly between electrical stimulation pulses. If the telemetry receiver detects any signal on its antenna between stimulation pulses, the telemetry receiver turns off the stimulation pulses momentarily in order to quiet the system to receive the downlink. After the telemetry signal is received, processed, and the resulting uplink response is sent via telemetry, the electrical stimulation pulses can then be turned on again. The window that looks for telemetry occurs every 2 milliseconds with a window width of about 220 microseconds. A wake-up burst that is at least 2 milliseconds long is then sent so that the 175 kiloHertz signal would be received by at least one of the reception windows.

A disadvantage of this technique is that electrical stimulation therapy might need to be stopped to allow for telemetry communication. If the telemetry communication duration is long (such as receiving large blocks of data from the device or downloading a new application into the implantable medical device), electrical stimulation therapy might be disabled for long periods and the side effects of not having electrical stimulation therapy enabled could impact the patient, e.g., a tremor could return for a tremor patient, pain could return for a pain patient, etc.

A technique used in implantable medical devices used in cardiac pacing is to interleave the telemetry data between electrical stimulation therapy pulses. Alternatively, pacing systems also attempt telemetry during therapy and, if the communication is unsuccessful, the system can retry the communication at a later time. Both of these methods can work well for cardiac pacing therapy, where the pulse rate of the electrical stimulation therapy is less than 2 Hertz. However, in typical neurostimulators, a pulse rate of 260 Hertz or higher for electrical stimulation therapy, so interleaving telemetry data or retrying when the electrical stimulation therapy corrupts data communication becomes impractical, as the data rate is greatly diminished.

BRIEF SUMMARY OF THE INVENTION

An embodiment of the present invention provides a system for telemetry communication with an implantable medical device concurrent with the delivery of therapeutic output to a patient.

The receiver used in an embodiment of the present invention provides a true differential input receiver and has extremely good common mode noise rejection. Common mode filtering was accomplished by splitting a single parallel tank tuning capacitor into two series capacitors with the midpoint referenced to ground. This provides common mode filtering because the energy coupled into the antenna from the delivery of the therapy is seen equally on both sides of the antenna, so the noise does not cause a different voltage at each end of the antenna.

Diodes are placed in parallel to the split capacitors for full wave rectification while providing a reference to ground and input circuit protection. The split capacitor design minimizes diode conduction and preserves tuning, therefore maximizing the signal on the antenna.

In some embodiments, the above design alone can be susceptible to differential noise (fields generated outside the device). To reduce susceptibility to differential noise filtering is incorporated in some embodiments of the invention. Filtering may use a fixed minimum threshold detector which prevents detection until a signal has reached a fixed voltage level or a dynamic threshold detector which prevents detection of signals at a certain percentage of the peak signal. These filters are processed in parallel with the incoming signal and combined at the end of the receiver channel resulting in a filtered signal output.

To increase the signal to noise ratio (which allows a higher success to communicate rate in a noisy environment by moving the programming head closer to the device), the receiver can operate on the voltage being provided on the receiving antenna if the voltage on the antenna is higher than the voltage supply provided by the battery in the device. In a preferred embodiment, a 4 volt regulated voltage is used to supply the energy to operate the receiver. When the voltage on the antenna rises above 4 volts, the regulator supply is switched to a voltage supply created off of the antenna. A Zener diode can be used to clip the voltage at 7 volts to keep an excessively high signal from damaging internal components in the receiver.

In an embodiment, the receiver also has a logarithmic front end, which allows the receiver to have a wide dynamic range of signal strengths.

This allows telemetry communication with an implanted medical device without interrupting electrical stimulation therapy. This prevents potential side effects that can occur when stopping and starting electrical stimulation therapy and allows successful emergency downlinks even if the programmer can not detect the uplink because of high noise levels.

In an embodiment, the present invention provides an implantable medical device having a therapy module providing a therapeutic output to a patient and a telemetry module, operatively coupled to the therapy module, providing bi-directional transcutaneous telemetry communication using a telemetry signal with an external device. An electromagnetic signal is associated with at least one of recharging of a rechargeable power source and providing the therapeutic output. the bi-directional transcutaneous communication occurs while the telemetry signal and the electromagnetic signal occur simultaneously.

In a preferred embodiment, the implantable medical device further comprises a rechargeable power source operatively coupled to the therapy module and wherein the electromagnetic signal is associated with recharging the rechargeable power source.

In a preferred embodiment, the rechargeable power is recharged using inductive coupling and wherein the electromagnetic signal arises from the inductive coupling.

In a preferred embodiment, the electromagnetic signal is associated with delivery of the therapeutic output.

In a preferred embodiment, the therapeutic output is an electrical stimulus signal and wherein the electromagnetic signal is derived, at least in part, from the electrical stimulus signal.

In a preferred embodiment, the bi-directional telemetry occurs while the telemetry signal and the electrical stimulus signal occur simultaneously.

In a preferred embodiment, the electromagnetic signal occurs during delivery of the therapeutic output.

In a preferred embodiment, the therapy module comprises a drug delivery module having a drug pump and wherein the electromagnetic is generated by the drug pump.

In a preferred embodiment, the electromagnetic signal is associated with an activity of the implantable medical device prefatory to delivery of the therapeutic output.

In a preferred embodiment, the implantable medical device comprises a defibrillator, wherein the therapeutic output comprises an electrical stimulus signal and wherein the electromagnetic signal is generated during charging of the implantable medical device in preparation for delivery of the electrical stimulus signal.

In an alternative embodiment, the present invention provides an implantable medical device for providing a therapeutic output to a patient having a therapy module providing a therapeutic output to a patient. An electromagnetic signal is associated with at least one of recharging of a rechargeable power source and providing the therapeutic output. An intermediate grounded receiving coil is adapted to receive a transcutaneous telemetry signal. A telemetry module, operatively coupled to the intermediate grounded receiving coil and to the therapy module, provides transcutaneous telemetry communication using the telemetry signal with an external device. The transcutaneous telemetry communication occurs while the telemetry signal and the electromagnetic signal occur simultaneously.

In a preferred embodiment, the secondary coil is a center grounded receiving coil.

In a preferred embodiment, the telemetry module is a dual channel threshold detector.

In a preferred embodiment, the telemetry module of the implantable medical device further is a differential amplifier operatively coupled to the receiving coil for receiving the transcutaneous telemetry communication and a common mode amplifier operatively coupled to the receiving coil.

In a preferred embodiment, the telemetry module further is a common mode amplifier operatively coupled to the receiving coil for a first one of the dual channel threshold detector and one of a differential trigger and a fixed threshold for a second one of the dual channel threshold detector.

In a preferred embodiment, the common mode amplifier is configured to utilize one of a low voltage trigger and a high voltage trigger.

In a preferred embodiment, the implantable medical device further comprises a rechargeable power source operatively coupled to the therapy module and wherein the electromagnetic signal is associated with recharging the rechargeable power source.

In a preferred embodiment, the rechargeable power is recharged using inductive coupling and wherein the electromagnetic signal arises from the inductive coupling.

In a preferred embodiment, the electromagnetic signal is associated with delivery of the therapeutic output.

In a preferred embodiment, the therapeutic output comprises an electrical stimulus signal and wherein the electromagnetic signal is derived, at least in part, from the electrical stimulus signal.

In a preferred embodiment, the electromagnetic signal occurs during delivery of the therapeutic output.

In another alternative embodiment, the present invention provides a system for providing a therapeutic output to a patient using the implantable medical device described herein and an external device configured for transcutaneous telemetry communication with the implantable medical device.

In another alternative embodiment, the present invention provides a method for providing a therapeutic output to a patient. The therapeutic output is provided to the patient with an implantable medical device wherein an electromagnetic signal is associated with at least one of recharging of a rechargeable power source and providing the therapeutic output. Bi-directional transcutaneous communication is conducted via via telemetry between the implantable medical device and an external device using a telemetry signal while the telemetry signal and the electromagnetic signal occur simultaneously.

DETAILED DESCRIPTION OF THE INVENTION

Embodiments of the present invention have usefulness in many different implantable medical devices. A preferred embodiment of the present invention is especially useful in an implantable medical device providing electrical stimulation therapy. An example of such a device, system and method is described in U.S. Pat. No. 6,505,077, Kast et al, Implantable Medical Device With External Recharging Coil Electrical Connection, the content of which are hereby incorporated by reference.

Figure 1:
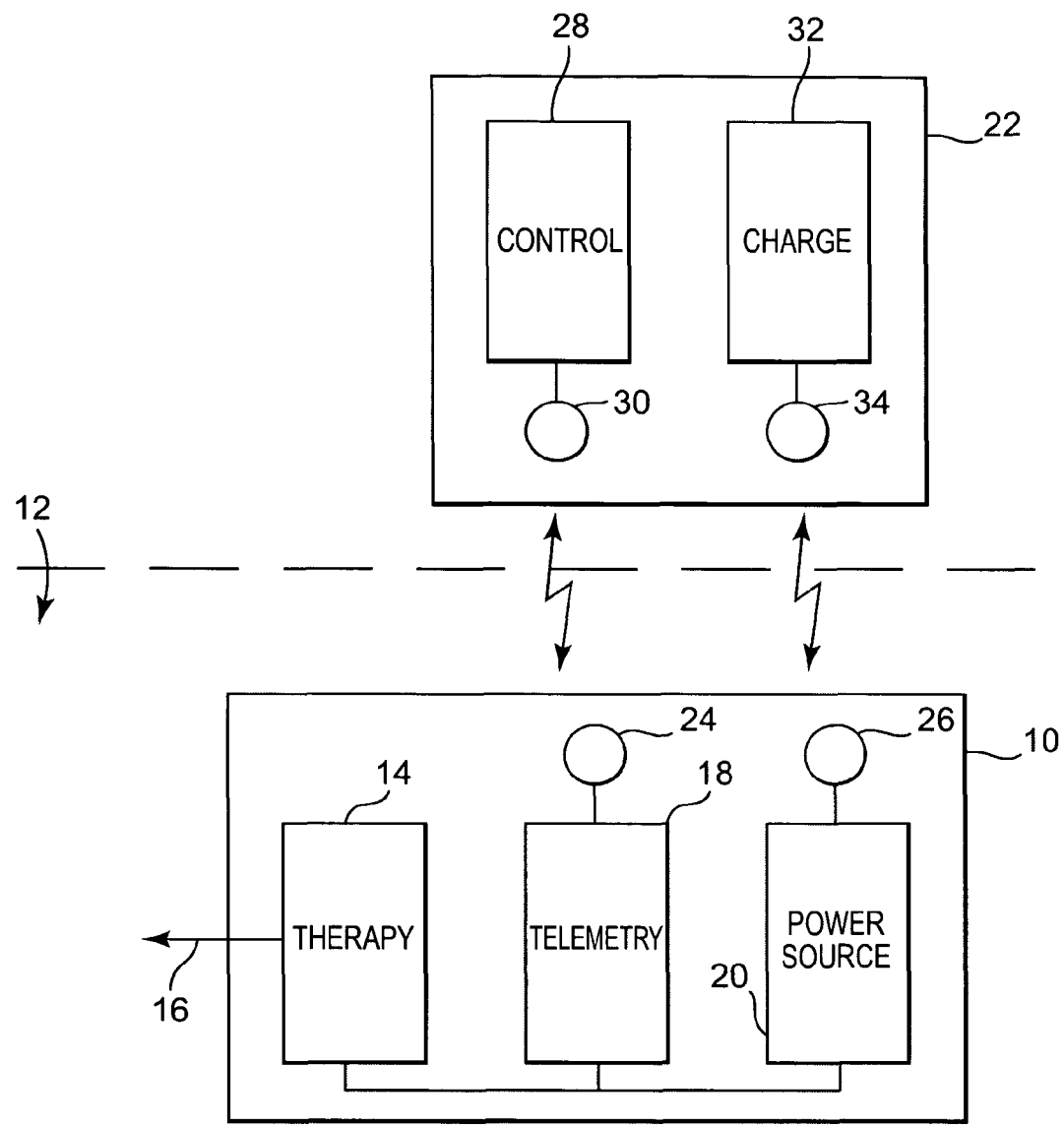
FIG. 1 is a block diagram of an implantable medical device used in conjunction with an external device.

A close-up diagrammatic view of implantable medical device 10 implanted into patient 12 is illustrated in FIG. 1. Implantable medical device 10 is generally composed of therapy module 14 which provides a therapeutic output 16 to patient 12, telemetry module 18 and power supply 20 providing electrical power to both therapy module 14 and telemetry module 18. In general, implantable medical device may by any of a variety of commonly available implantable medical devices providing a therapeutic output 16 to a patient 12. Examples, of such devices include, but are not limited to, implantable neurostimulators, drug pumps, cardiac pacemakers and defibrillators and other devices. Therapy modules 14 associated with such implantable medical devices 10 are well known in the industry.

Telemetry module 18 may be any of a variety of commonly known and available modules for supporting transcutaneous communication between implantable medical device 10 and external device 22 which is generally used for controlling or programming implantable medical device 10 or for providing information regarding the condition, state, status or history of implantable medical device 10 or information relating to patient 12. Telemetry techniques are commonly known in the industry and typically involve the transmission and reception of an electromagnetic wave between implantable medical device 10 and external device 22. Any of a number of commonly available telemetry schemes may be utilized.

Power source 20 may be any of a variety of commonly known and available power supply such as chemical batteries and, in particular, rechargeable batteries. Power source 20 may provide electrical power to both therapy module 14 and telemetry module 18 although it is to be recognized and understood that therapy module 14 and telemetry module 18 may have their own separate power sources.

Telemetry antenna 24, coupled to telemetry module 18, is adapted to receive electromagnetic signals sent transcutaneously from external device 22 and to transmit electromagnetic signals toward external device 22.

Power antenna 26, coupled to power source 20, is adapted to receive electromagnetic energy from external device 22 for the purpose of supplying energy to implantable medical device 10, including, but not limited to, recharging of power source 20.

While shown separately, telemetry antenna 24 may be nested with power antenna 26 or, in an alternative embodiment, telemetry antenna 24 may be combined with power antenna 26.

External device 22 contains control module 28 which is coupled to telemetry antenna 30 and is adapted to either control or program implantable medical device 10 or provide information about implantable medical device 10 or patient 12 through telemetry communication with implantable medical device 10 using transcutaneous electromagnetic signals between telemetry antenna 30 of external device 22 and telemetry antenna 24 of implantable medical device.

External device 22 also contains charging module 32 which is coupled to charging antenna 34 and is adapted to transmit electromagnetic energy to power source 20 of implantable medical device 10 through power antenna 26. Such transcutaneous electromagnetic energy transfer is conventional and well known in the art.

It is to be noted that while external device 22 is shown as containing both control module 28 and charging module 32, it is to be recognized and understood that the control and/or programming functions and energy transfer function of external device 22 could be implemented in separate and independent devices.

Figure 2:
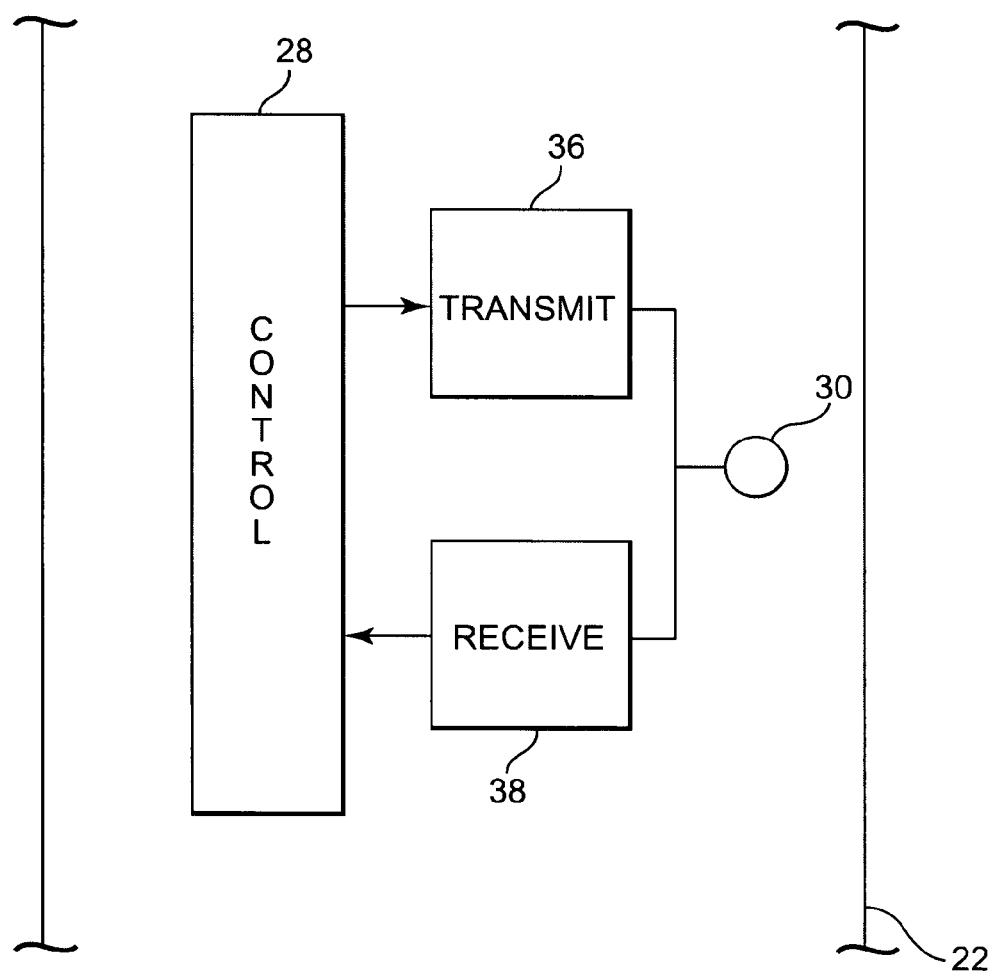
FIG. 2 is a more detailed block diagram of a portion of the external device.

FIG. 2 illustrates a partial block diagram view of external device 22 showing control module 28 and telemetry antenna 30. Control module 28 operates to communicate bi-directionally with implantable medical device 10 through transmit module 36 and receive module 38. Transmit module 36 is responsible for providing data and communication formatting for communication from external device 22 to implantable medical device 10. Receive module 38 is responsible for decoding transmitted information received from implantable medical device 10. Transmit module 36 and receive module 38 are illustrated coupled to a single telemetry antenna 30. It is to be recognized and understood that transmit module 36 and receive module 38 may utilize a common telemetry antenna 30 or may utilize separate and independent antennas.

Figure 3:
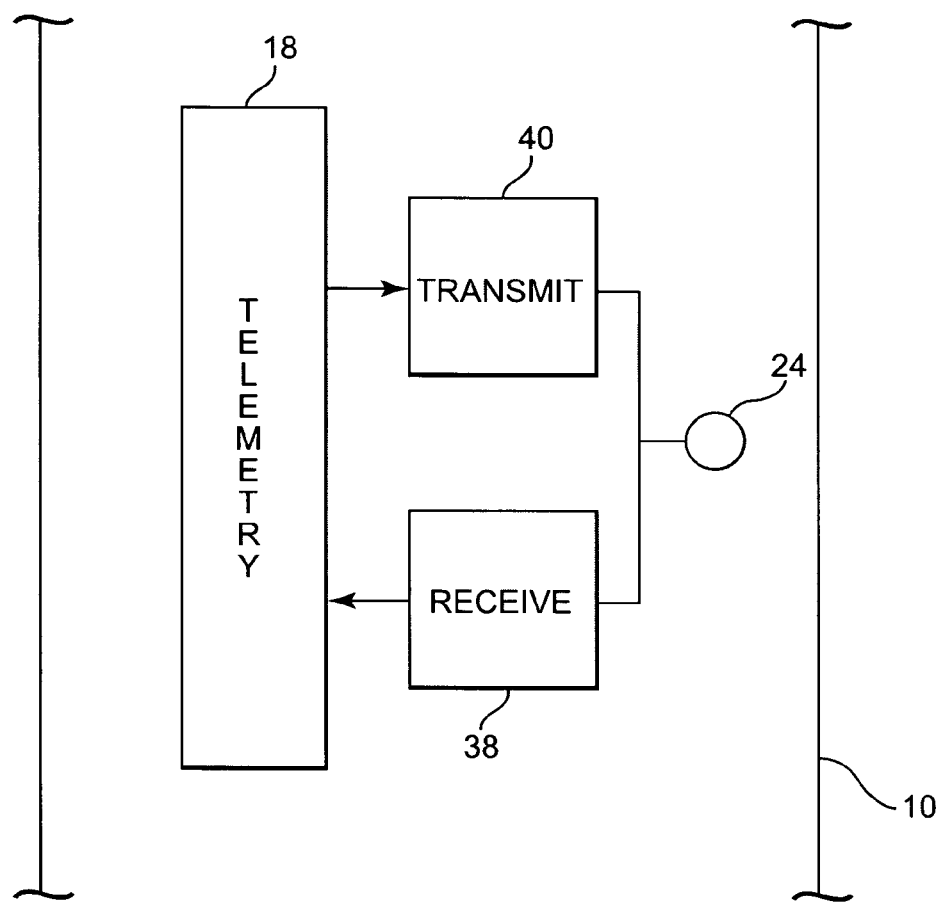
FIG. 3 is a more detailed block diagram of a portion of the implantable medical device.

FIG. 3 illustrates a partial block diagram view of implantable medical device 10 showing telemetry module 18 and telemetry antenna 24. Telemetry module 18 operates to communicate bi-directionally with external device 22 through transmit module 40 and receive module 42. Transmit module 40 is responsible for providing data and communication formatting for communication from implantable medical device 10 to external device 22. Receive module 42 is responsible for decoding transmitted information received from external device 22. Transmit module 40 and receive module 42 are illustrated coupled to a single telemetry antenna 24. It is to be recognized and understood that transmit module 40 and receive module 42 may utilize a common telemetry antenna 24 or may utilize separate and independent antennas.

Implantable medical device 10 may generate significant electromagnetic energy in its normal operation. Such electromagnetic energy may be generated, for example, in the provision of an electrical stimulus pulse or signal train in a neurostimulator. Even drug pumps may produce significant electromagnetic energy in the provision of a medicant to patient 12 since such devices may employ an electrically operated motor or pump which may produce electromagnetic signal or noise spikes during their operation. Alternatively or in addition, substantial electromagnetic is associated with the provision of transcutaneous energy transfer to either supply power to implantable medical device 10 or to recharge power source 20.

In such situations, electromagnetic noise may drown out telemetry signals passing either from external device 22 to implantable medical device 10 or vice versa. Implantable medical device 10 employs receive module 42 adapted to enable to receipt of intelligible telemetry information from external device 22 even while implantable medical device 10 is generating significant electromagnetic signals through the provision of therapeutic output 16, e.g., an electrical stimulus or noise associated with a drug pump, or while implantable medical device 10 is receiving electromagnetic energy from charging module of external device 22.

Figure 4:
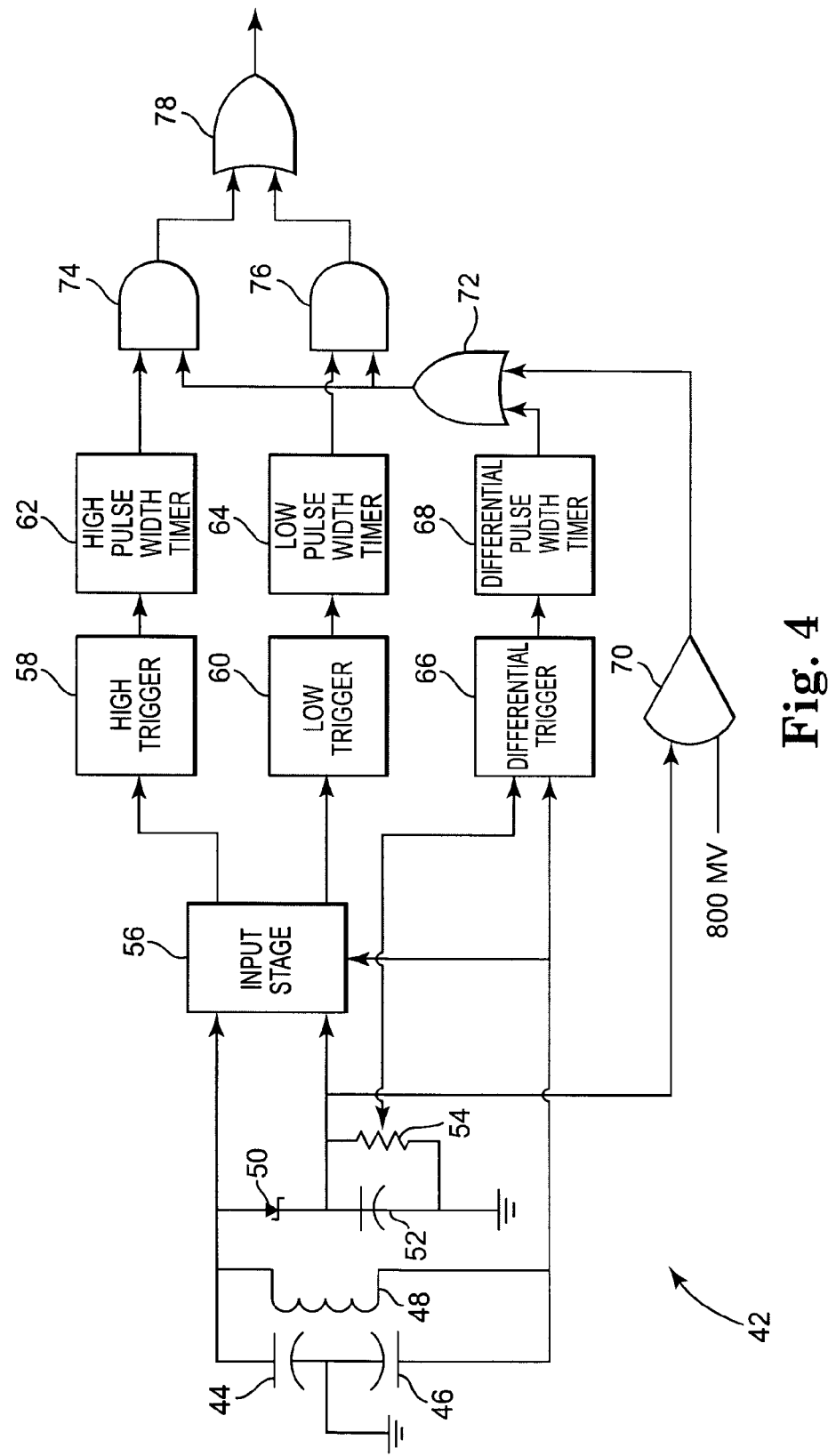
FIG. 4 is a schematic diagram of the receive module in implantable medical device.

Capacitors 44 and 46 (see FIG. 4) are center grounded and coupled to receiving coil 48. Zener diode 50, capacitor 52 and resistor 54 along with center grounded capacitors 44 and 46 provide a floating reference level around which telemetry signals appearing at receiving coil 48 may be detected. Receive module 42 operates to produce a digital "one" provided that the amplitude of the oscillating telemetry signal appearing on center-grounded receiving coil 48 are above a predetermined level of the floating reference level.

Input stage 56 provides a common mode amplifier feeding both high trigger circuit 58 and low trigger circuit 60. High trigger circuit 58 is fed to a high pulse width timer 62 to provide a known minimum pulse width output from high trigger circuit 58. Low pulse width timer circuit 64 similarly provides a known minimum pulse output from low trigger circuit 60.

Dual high and low trigger circuits 58 and 60 provide a dual channel threshold detector.

Receive module 42 also contains differential amplifier 66 providing a differential output from receiving coil 48 adjustable from adjustable resistor 54. Differential pulse width timer 68 provides a known pulse minimum width output from differential amplifier 66.

Common mode amplifier 70 is referenced to a constant voltage, in this case 800 millivolts.

The output of common mode amplifier 70 is "ORed" with the output from differential pulse width timer 68 in OR gate 72. In other words, OR gate 72 passes a high signal whenever either the output from common mode amplifier 70 or differential pulse width timer 68 is high.

The output of each of high pulse width timer 62 and low pulse width timer 64 is "ANDed" with the output from OR gate 72 in AND gates 74 and 76, respectively. In other words, the output from AND gate 74 is high whenever the outputs from both high pulse width timer 62 and OR gate 72 is high. Similarly, the output from AND gate 76 is high whenever the outputs from both low pulse width timer 64 and OR gate 72 is high.

The outputs of OR gates 74 and 76 are "ORed" in OR gate 78. The result is that receive module 42 passes a high signal whenever the output of either high trigger circuit 58 or low trigger circuit 60 is if either the output of differential trigger 66 or common mode amplifier is high.

Figure 5:
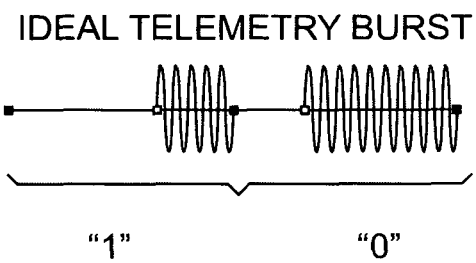
FIG. 5 shows an ideal telemetry burst.

In a preferred embodiment, the telemetry signal broadcast by the external device 22 has a base band of 4.4 kilobits per second and a carrier frequency of 175 kiloHertz. The telemetry signal is amplitude modulated. One's and zero's are communicated using a psuedo-AM (amplitude modulation) communication scheme where the length of each pulse and the time in between pulses determines if the pulse represents a 1 or a 0. FIG. 5 shows an ideal Telemetry N burst with the 1's and the 0's labeled to show timing differences between the two.

Figure 6:
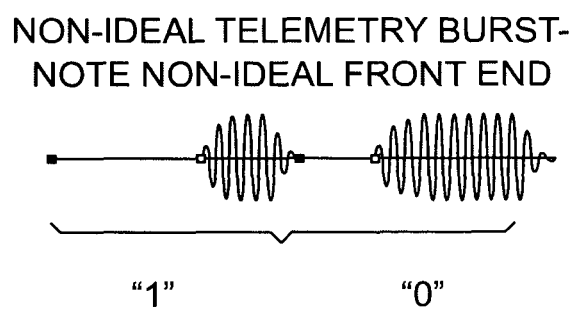
FIG. 6 shows an non-ideal telemetry burst.

The external device 22, however, may not produce an ideal telemetry burst. A non-ideal telemetry burst may have a rise time where the beginning cycles do not reach full amplitude for a certain amount of time. FIG. 6 shows an example of a non-ideal telemetry burst.

Receive module 42 provides peak tracking and dynamic threshold control. The first function is tracking the peak of the received telemetry signal. A RC time constant is set to hold this peak value for a certain amount of time in between bursts and after the end-of-message signal. The second function is to set the dynamic threshold. This is accomplished by taking a certain percentage of the peak voltage (determined by the peak tracking function) and sending it on, in the form of an offset, to the trigger circuits 58 and 60.

The peak of the received telemetry signal is tracked using the peak tracker. The peak voltage is set-up on the hybrid capacitors 44 and 46. A time constant is involved in setting up the peak voltage because of the RC time constant.

Figure 7:
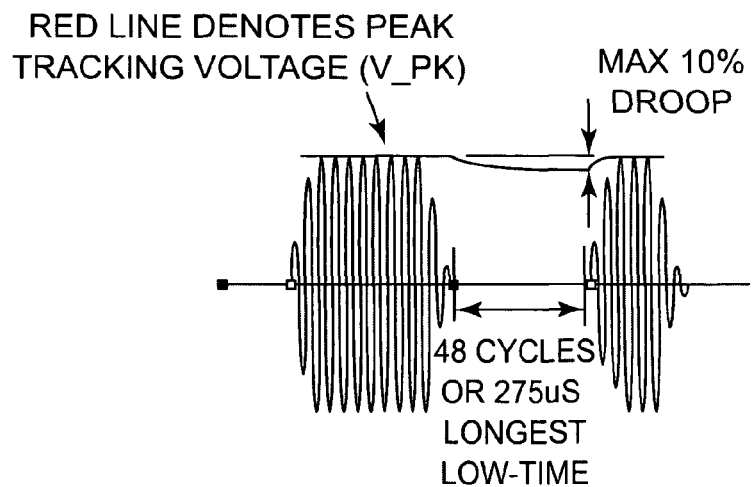
FIG. 7 illustrates in between burst peak tracker operation.

The peak tracker is designed to hold the dynamic threshold to a certain percentage of the peak voltage in between bursts. It is the intent of the peak tracker to only let the peak voltage set on the capacitor drop 10% in between bursts. The worst-case ~2 millisecond time constant allows the peak tracker to only lose 10% of the peak value during the longest low-time of the message. FIG. 7 illustrates in between burst peak tracker operation.

The longest low-time in a message is 48 cycles, or 275 microseconds, just before the 16 cycle end-of-message burst. If we again look to the equation $$0.9\ V_0 = V_0 e^{\frac{-275uS}{\tau}}$$

and set V to 90% of $V_O$ and set the time to be 275 microseconds we can solve for the time constant needed to keep the peak tracker at 90% of the peak signal in between bursts.

After the message is finished the voltage on capacitors 44 and 46 will clear according to the time constant as well. The capacitors 44 and 46 will be defined as cleared once it has decayed down to 10% of its original value.

Figure 8:
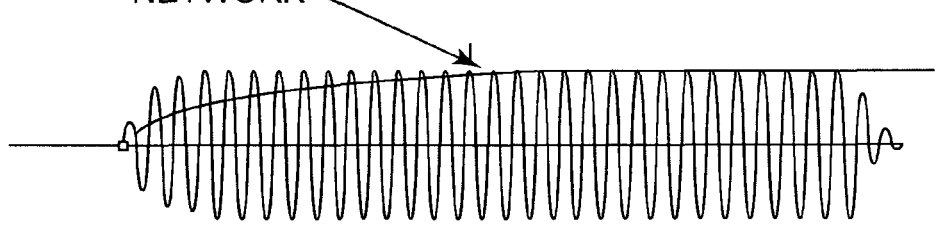
FIG. 8 illustrates a peak tracking signal on a telemetry burst.

FIG. 8 shows a reasonable telemetry burst with an exponentially rising peak tracking signal.

The dynamic threshold control uses the voltage created by the peak voltage detector and takes some percentage of that voltage. The percentage of the peak voltage is used as the new receiver threshold during a message. The dynamic threshold allows communication in a noisy environment by increasing the detection threshold when there is sufficient signal on the coil.

The design has the option of changing the percentage of the peak received voltage that the dynamic threshold will rise to is adjustable resistor 54.

The fixed threshold control block controls the fixed threshold level. This block uses the peak of the signal measured using the peak signal from the peak detector and dynamic threshold control block and compares it to a fixed threshold level set for a specific device. If the peak of the signal is larger than the fixed threshold level the receiver's comparator block is activated using a signal. If the peak signal is smaller than the fixed threshold level of the receiver the comparator block is de-activated.

Figure 9:
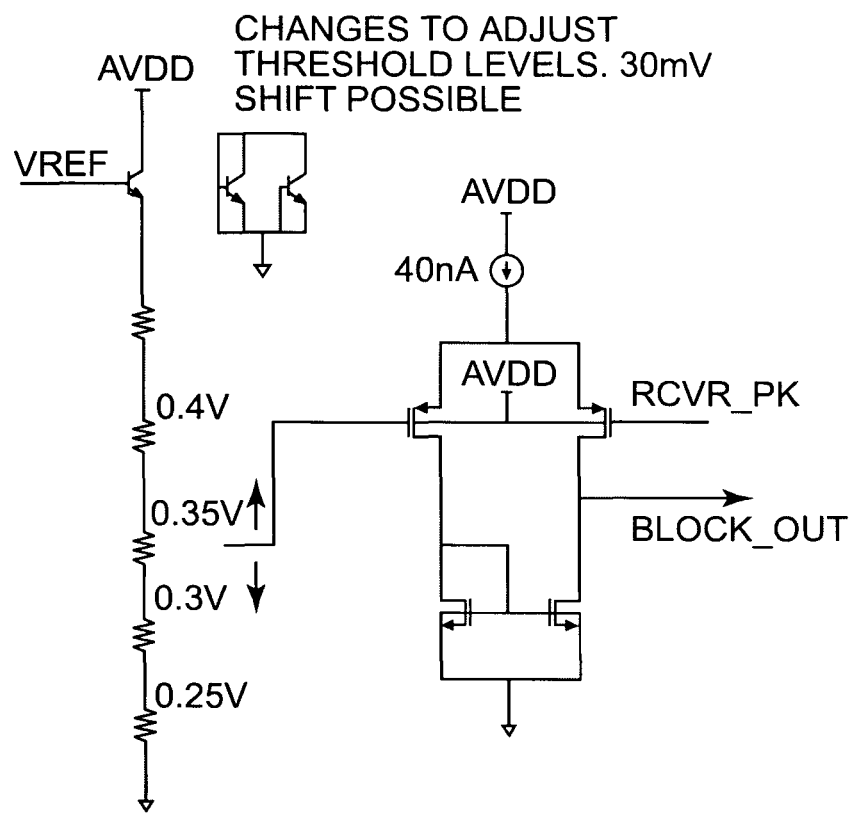
FIG. 9 is a fixed threshold control block circuit diagram.

FIG. 9 shows that the fixed threshold level is realized by sending a current through a resistor and measuring the voltage across that resistor. This voltage is then compared to the peak voltage measured in the peak tracker and dynamic threshold control.

As noted in the purpose statement, receive module 42 senses and conditions the telemetry antenna voltage received at the physical layer and creates a digital signal that represents the telemetry signal at the data-link layer. Receive module 42 also provides the signal-to-noise ratio necessary to maintain operation during stimulation.

A peak tracker tracks the peak of the antenna voltage across Zener diode 50. A time constant sets the growth and decay properties of the peak voltage as compared to the telemetry (or noise) burst. The voltage created using the RC is considered the peak of the telemetry burst. This peak voltage is then used in the fixed threshold to determine if the telemetry burst is above the fixed threshold. The peak voltage is also used to set the dynamic threshold.

The peak tracker block also provides a bias for input stage 56.

Input stage 56 acts as a pre-amplifier with non-linear compression and gain for the high and low signal paths of the receive module 42. Input stage 56 amplifies the differential and filters the common mode signal between both sides of the antenna. These amplified signals are both sent directly to the high and low trigger circuits (58 and 60) for further processing. When the signal level is greater, the signal is sent to the low channel trigger circuit 60. When the signal level is less, the signal is sent to the high channel trigger circuit 58.

Input stage 56 also provides a band pass function.

Common mode amplifier 70 provides a fixed threshold control ensuring that a signal below the fixed threshold does not cause the receive module 42 to trip. The fixed threshold control uses a comparator 70 to compare the peak voltage of the received signal from the peak tracker to the fixed threshold voltage (800 millivolts). If the peak voltage of the received signal is larger than the fixed threshold level comparator 70 will be activated. If the peak of the received signal is smaller than the fixed threshold level the comparator 70 will be de-activated.

High and low trigger circuits 58 and 60 are identical and are basically Schmitt triggers that trigger when one input goes negative or positive relative to the other input. The high and low trigger circuits are then able to create a digital signal that should represent the carrier frequency of 175 kiloHertz.

Figure 10:
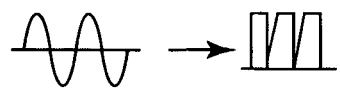
FIG. 10 illustrates a trigger signal flow diagram.

The basic signal flow is shown in FIG. 10.

The differential noise trigger 66 provides a dynamic threshold to filter out low-level noise when the signal level is large enough.

Figure 11:
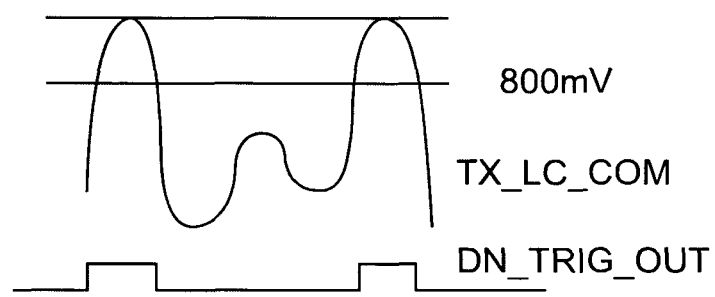
FIG. 11 illustrates differential trigger operation.

FIG. 11 shows how the differential noise trigger 66 ignores the low-level noise when the signal level seen on receive coil 48 is large enough.

The high and low pulse-width timers (62 and 64) are identical and perform the same function for their respective signal paths. They are re-triggerable time-out timers that use the output of the triggers (high and low respectively.)

The pulse-width timers (62 and 64) effectively filter out the carrier frequency of 175 kiloHertz and create a 4.4 kilobits per second signal. The timers accomplish this by looking for the input signal to go high (2 volts) and setting a timer. As soon as the input signal goes high the timer is set and the output signal goes high. If the input signal is high when the timer has expired the timer will reset and the output signal will remain high. If the input signal is low when the timer expires the output signal will go low.

Figure 12:
FIG. 12 illustrates a pulse width timer signal flow diagram.
Figure 13:
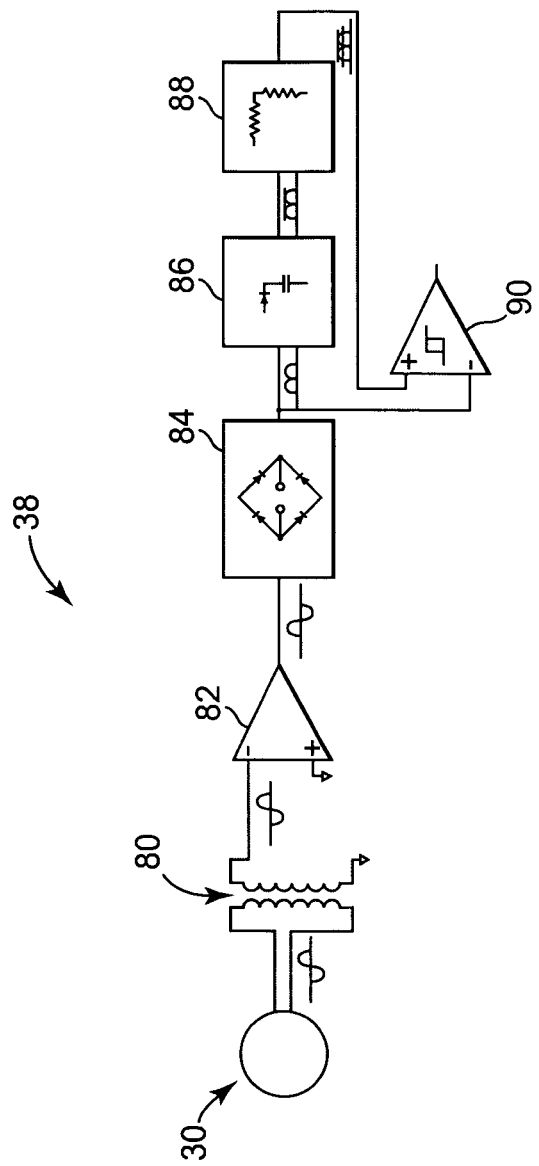
FIG. 13 is a schematic block diagram of a receive module in an external device.

FIG. 12 shows the signal flow of the pulse width timers 62 and 64. The signal from the triggers is taken and the pulse-width timer creates the 4.4 kilobit per second signal.

Differential pulse width timer 68 performs the same function for differential trigger 66 as the high and low pulse width timers (62 and 64) do for high and low triggers (58 and 60) and is also re-triggerable.

Differential trigger 66 acts as a switch to turn on the differential noise filtering. Differential trigger 66 compares a percentage of the voltage of the received signal across receive coil 48 to a predetermined voltage level. When the received voltage is larger than a predetermined voltage value, differential filtering is enabled. Differential filtering filters out low-level noise when there is a large amplitude on the received telemetry signal.

After a transmission has occurred, the capacitor on the peak tracker should be cleared. If the capacitor is not cleared, the receive module 42 could ignore a telemetry downlink because the dynamic threshold would be set high because of a voltage on the peak tracker capacitor. The capacitor is shorted when the transmitter is inactive and the receiver is active.

Uplink telemetry communication is achieved by utilizing transmit module 40 in implantable medical device 10 and receive module 38 in external device 22. Transmit module 40 is conventional in nature and well known in the art using conventional techniques.

Receive module 38 in external device 22 is much more straight forward than receive module 42 in implantable medical device. Telemetry antenna 30 is coupled directly to transformer 80. The signal from transformer 80 is amplified in amplifier 82 and full wave rectified in full wave rectifier 84. Peak detector 86 uses a series diode and a parallel capacitor to detect a peak value. A threshold is established is threshold block 88 consisting of a voltage divider. Comparator 90 compares the signal from full wave rectifier 84 and the signal from the threshold block 88 to produce a positive output when the full wave rectified signal is above the threshold signal.

Operation of any circuitry in implantable medical device consumes power. Since size and longevity are usually primary concerns for implantable medical devices, any power savings can yield either size or longevity improvements or both. The telemetry module 18 as well as transmit module 40 and receive module 42 consume power in implantable medical device 10. This is particularly true since many components contained in the transmit and receive modules 40 and 42 are analog components and, as such, may require voltages and currents in excess of that typically required by digital components.

Figure 14:
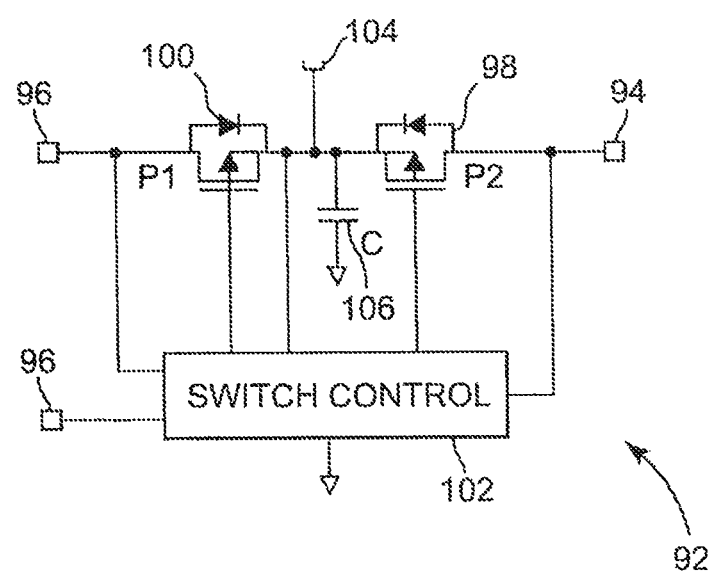
FIG. 14 is a schematic diagram is a power supply switched voltage circuit.

Switched supply block 92 provides power to one or more of telemetry module 18, transmit module 40 and/or receive module 42 from the telemetry signal when implantable medical device 10 is receiving a telemetry signal. Switched supply block 92 provides power to circuits that need a high-voltage power supply when high voltage levels are seen on telemetry antenna 24 while receiving a telemetry transmission. Switched supply block 92 illustrated in FIG. 14 is a two-FET well-switcher that places the voltage from either the internal power source or switched supply from the telemetry antenna depending on which one is larger. Peripheral circuitry has been added to the well-switcher to ensure proper operation under all system conditions.

Switched supply block 92 is a well switcher that chooses the higher of the two voltages to supply a number of circuits in receive module 42. Switched supply block 92 allows the receive module 42 to use the energy on the receive coil 48 to power the receive module 42 during telemetry reception when the received signal amplitude creates a voltage that is larger than the internal power source voltage.

Switched supply block 92 has hysteresis around 4.0 volts. When the voltage on receive coil 48 is increasing the switched supply block 92 will begin using this voltage as a supply voltage as soon as it is greater than the voltage of the internal power source.

Voltage 94 from the internal power source is available to switched supply block 92. Also available is voltage 96 from receive coil 48. Voltage 94 from the internal power source of implantable medical device 10 is fed to field effect transistor (FET) 98 while voltage 96 from receive coil 48 is fed to field effect transistor (FET) 100. Switch control logic 102 is coupled to both voltages 94 and 96 and controls FETs 98 and 100 to effectively switch between voltage sources depending upon which voltage source is higher. The switched supply block 92 output voltage 104 is taken from the outputs of both FETs 98 and 100 and stabilized with capacitor 106.

The contents of provisional U.S. application Ser. No. 60/589,393, filed Jul. 20, 2004, and provisional U.S. application Ser. No. 60/589,950, filed Jul. 21, 2004, are hereby incorporated by reference.

Thus, embodiments of the concurrent delivery of treatment therapy with telemetry in an implantable medical device are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device implantable within a patient, comprising:
   a telemetry module adapted to provide bi-directional transcutaneous telemetry communication using a telemetry signal with an external device;
   a circuit adapted to perform transcutaneous recharging of a rechargeable power source, wherein an electromagnetic signal is generated by said transcutaneous recharging of a rechargeable power source;
   wherein said bi-directional transcutaneous communication occurs while said telemetry signal and said electromagnetic signal occur simultaneously; and
   wherein said telemetry module is adapted to prevent said electromagnetic signal from corrupting said telemetry signal.

2. An implantable medical device as in claim 1 wherein said rechargeable power is recharged using inductive coupling and wherein said electromagnetic signal arises from said inductive coupling.

3. An implantable medical device as in claim 1 further comprising a therapy module adapted to provide a therapeutic output to the patient.

4. An implantable medical device as in claim 3 wherein said therapeutic output comprises an electrical stimulus signal.

5. An implantable medical device as in claim 3 wherein said electromagnetic signal further occurs during delivery of said therapeutic output.

6. An implantable medical device as in claim 3 wherein said electromagnetic signal is further associated with an activity of said implantable medical device prefatory to delivery of said therapeutic output.

7. A system, comprising;
   said implantable medical device as in claim 1; and
   an external device configured for transcutaneous telemetry communication with said implantable medical device.

8. An implantable medical device as in claim 1, wherein said circuit adapted to perform an operation associated with transcutaneous recharging is coupled to a center grounded receiving coil.

9. An implantable medical device as in claim 1 wherein said telemetry module comprises a dual channel threshold detector.

10. An implantable medical device as in claim 9 wherein said telemetry module further comprises a common mode amplifier operatively coupled to a receiving coil for a first one of said dual channel threshold detector and one of a differential trigger and a fixed threshold for a second one of said dual channel threshold detector.

11. An implantable medical device as in claim 10 wherein said common mode amplifier is configured to utilize one of a low voltage trigger and a high voltage trigger.

12. An implantable medical device as in claim 1 wherein said telemetry module further comprises a differential amplifier operatively coupled to a receiving coil for receiving said transcutaneous telemetry communication.

13. An implantable medical device as in claim 12, further comprising a common mode amplifier operatively coupled to said receiving coil.

14. An implantable medical device, comprising;
   a circuit configured to transcutaneously recharge a rechargeable power source of the implantable medical device, wherein an electromagnetic signal is generated by the transcutaneous recharging of the rechargeable power source;
   an intermediate grounded receiving coil adapted to receive a transcutaneous telemetry signal; and
   a telemetry module, operatively coupled to said intermediate grounded receiving coil and configured to provide bi-directional transcutaneous telemetry communication using said telemetry signal with an external device;
   wherein said transcutaneous telemetry communication occurs while said telemetry signal and said electromagnetic signal occur simultaneously; and
   wherein said telemetry module is adapted to prevent said electromagnetic signal from corrupting said telemetry signal.

15. An implantable medical device as in claim 14, further comprising a secondary coil, wherein said secondary coil is a center grounded receiving coil.

16. An implantable medical device as in claim 14 wherein said telemetry module comprises a dual channel threshold detector.

17. An implantable medical device as in claim 16 wherein said telemetry module of said implantable medical device further comprises a differential amplifier operatively coupled to said receiving coil for receiving said transcutaneous telemetry communication and a common mode amplifier operatively coupled to said receiving coil.

18. An implantable medical device as in claim 16 wherein said telemetry module further comprises a common mode amplifier operatively coupled to said receiving coil for a first one of said dual channel threshold detector and one of a differential trigger and a fixed threshold for a second one of said dual channel threshold detector.

19. An implantable medical device as in claim 18 wherein said common mode amplifier is configured to utilize one of a low voltage trigger and a high voltage trigger.

20. An implantable medical device as in claim 14 wherein said implantable medical device further comprises a therapy module configured to deliver therapeutic output.

21. An implantable medical device as in claim 20 wherein said electromagnetic signal is further associated with delivery of said therapeutic output.

22. An implantable medical device as in claim 21 wherein said therapeutic output comprises an electrical stimulus signal and wherein said electromagnetic signal is further derived, at least in part, from said electrical stimulus signal.

23. An implantable medical device as in claim 21 wherein said electromagnetic signal occurs during delivery of said therapeutic output.

24. An implantable medical device as in claim 14 wherein said rechargeable power is recharged using inductive coupling and wherein said electromagnetic signal arises from said inductive coupling.

25. A method, comprising the steps of:
   transcutaneously recharging a rechargeable power source of an implantable medical device wherein an electromagnetic signal is generated by said transcutaneously recharging of said implantable medical device; and bi-directionally transcutaneously communicating via telemetry between said implantable medical device and an external device using a telemetry signal while said telemetry signal and said electromagnetic signal occur simultaneously, and wherein said telemetry module is adapted to prevent said electromagnetic signal from corrupting said telemetry signal.

26. A method as in claim 25 wherein recharging said rechargeable power source comprises recharging using inductive coupling and wherein said electromagnetic signal arises from said inductive coupling.

27. A method as in claim 25 wherein said electromagnetic signal is further associated with delivery of said therapeutic output.

28. A method as in claim 27 wherein said therapeutic output comprises an electrical stimulus signal and wherein said electromagnetic signal is derived, at least in part, from said electrical stimulus signal.

29. A method as in claim 27 wherein said electromagnetic signal is associated with an activity of said implantable medical device prefatory to delivery of said therapeutic output.

30. A method as in claim 29 wherein said implantable medical device comprises a defibrillator, and wherein said electromagnetic signal is generated, at least in part, during charging of said implantable medical device in preparation for delivery of said electrical stimulus signal.

31. A method as in claim 25 wherein said bi-directionally transcutaneously communicating via telemetry comprises communicating via an intermediate grounded receiving coil for receiving a transcutaneous telemetry signal.

32. A method as in claim 31 wherein said intermediate ground receiving coil comprises a center grounded receiving coil.

33. A medical device implantable within a patient, comprising:
a circuit adapted to transcutaneously recharge a rechargeable power source of the medical device, said transcutaneous recharging generating an electromagnetic signal and
a telemetry module adapted to perform bi-directional telemetry communication via a telemetry signal while said electromagnetic signal is occurring, and said telemetry module is adapted to prevent corruption of said telemetry signal by said electromagnetic signal.

34. A medical device as in claim 33, further comprising a therapy module configured to deliver therapy; and
wherein said electromagnetic signal is further associated with an activity of the medical device prefatory to delivery of said therapy.

35. A medical device as in claim 34 the medical device comprises a defibrillator, wherein said therapy comprises an electrical stimulus signal and wherein said electromagnetic signal is further generated during charging of the medical device in preparation for delivery of said electrical stimulus signal.

36. A medical device as in claim 34, wherein said therapy module is configured to deliver neurostimulation therapy.

37. A system, comprising;
said medical device as in claim 33; and
an external device configured for transcutaneous telemetry communication with said medical device.

38. A medical device as in claim 33 wherein said electromagnetic signal comprises a signal having a frequency greater than 2 Hz.

* * * * *

UNITED STATES PATENT AND TRADEMARK OFFICE
CERTIFICATE OF CORRECTION

| | | |
|---|---|---|
| PATENT NO. | : 8,428,712 B2 | Page 1 of 1 |
| APPLICATION NO. | : 11/185525 | |
| DATED | : April 23, 2013 | |
| INVENTOR(S) | : Davis et al. | |

It is certified that error appears in the above-identified patent and that said Letters Patent is hereby corrected as shown below:

On the Title Page

Item 57 - Abstract - Line 1: "and implantable medical for concurrently" should read --an implantable medical device for concurrently--

Item 57 - Abstract - Line 8: "is conducted via via" should read --is conducted via--

In the Claims

Col. 12, Line 6: "device,comprising;" should read --device, comprising:--

Col. 14, Line 25: "A system comprising;" should read --A system comprising:--

Col. 14, Line 29: "as in claim 33 wherein" should read --as in claim 33, wherein--

Signed and Sealed this
Second Day of July, 2013

Teresa Stanek Rea
*Acting Director of the United States Patent and Trademark Office*